United States Patent [19]

Landis

[11] Patent Number: 5,682,608
[45] Date of Patent: Nov. 4, 1997

[54] ARTICULATING VISOR APPARATUS

[75] Inventor: Timothy J. Landis, Loomis, Calif.

[73] Assignee: OP-D-OP, Inc., Roseville, Calif.

[21] Appl. No.: 671,700

[22] Filed: Jun. 28, 1996

[51] Int. Cl.$^6$ .................................................. A61F 9/00
[52] U.S. Cl. ............................... 2/12; 2/171; 2/209.3
[58] Field of Search .............................. 2/12, 15, 171, 2/183, 209.3, 209.4, 418

[56] References Cited

U.S. PATENT DOCUMENTS

| | | |
|---|---|---|
| 3,383,707 | 5/1968 | McNeill . |
| 5,131,094 | 7/1992 | Ackerman .................................. 2/12 |
| 5,503,497 | 4/1996 | Landis et al. . |

Primary Examiner—Diana Biefeld
Attorney, Agent, or Firm—John P. O'Banion

[57] ABSTRACT

A head worn visor apparatus having a headband, forwardly disposed shade, and a pair of rearwardly disposed elongated support arm assembliles having movable portions which are positionally adjustable to provide increased wearer comfort. The support arm assemblies each include a generally fixed forward support arm and an articulating segment and/or head gripping region pivotally coupled to the support arm. Preferably, cylindrical posts are included on the ends of the support arms, and sockets which pivotally engage the posts are included on the articulating portions.

5 Claims, 6 Drawing Sheets

ARTICULATING VISOR APPARATUS

BACKGROUND OF THE INVENTION

1. Field of the Invention

The present invention pertains generally to head worn visors and like devices, and more particularly to a visor apparatus having pivotally adjustable support arms and support pads which allow for adjustment of the visor to accommodate the wearer's head.

2. Description of the Background Art

Head worn visors are frequently utilized by golfers, tennis players, joggers, and other persons engaged in outdoor activities to reduce glare to the eyes and to prevent sunburn. Head worn visors are also commonly used in dental, medical and other professions to support face shields, eye shields, lights, reflectors, mirrors, magnifying optics, tinted glass or other apparatus from a wearer's head.

Conventional head worn visors typically comprise a headband with a forwardly disposed bill or shade and a pair of rearwardly disposed resilient arms which partially encircle and tensionally engage the sides of a wearer's head in order to hold or support the visor on the wearer's head. In another typical arrangement, the rearwardly disposed arms generally encircle the wearer's head and are coupled or joined together in the back of the wearer's head.

The aforementioned conventional visor types share a common deficiency; they are uncomfortable to wear, particularly for extended periods of time. In order to minimize discomfort, the visor must be frequently repositioned. This problem is most readily apparent with head worn visor devices having resilient, rearwardly disposed arms which tensionally engage the wearer's head, since the amount of force or tension applied by the resilient arms to the wearer's head generally cannot be controlled or adjusted, and the force or tension is applied to a relatively small area of the wearer's head. This is a particular problem for physicians, dentists, welders, and other persons who rely on face shields or other devices supported by a head worn visor since these persons frequently have both hands occupied in difficult or complex procedures and cannot free their hands to positionally adjust the head visor to a new position to increase comfort.

Accordingly, there is a need for a head worn visor apparatus which provides for positional control of rearwardly disposed tails, which allows adjustment of the amount of tension or force exerted by the tails against the sides of the wearer's head, and which allows control of the surface area of the rearward tails which are in contact with the wearer's head. The present invention satisfies these needs, as well as others, and generally overcomes the deficiencies present in the background art.

SUMMARY OF THE INVENTION

The present invention pertains to a head worn visor apparatus which provides increased wearer comfort. In general terms, the invention comprises a headband, a forwardly disposed bill or shade coupled to the headband, and a pair of rearwardly disposed support arms assemblies coupled to the headband. Each support arm assembly includes a head gripping pad and articulating means for positionally adjusting the head gripping pad relative to the support arm. Additionally, each support arm assembly can include a fixed portion and an articulating portion, and articulating means for positionally adjusting the articulating portion relative to the fixed portion.

By way of example and not of limitation, a head worn visor in accordance with the present invention includes first and second elongated, spaced apart support arms extending in the rearward direction. In a first embodiment of the invention, a head gripping pad is pivotally coupled to the end of each support arm by an articulating adjustment means to form the support arm assembly. In a second embodiment, the first and second support arms each preferably include a fixed forward portion, a pivotally adjustable rearward portion coupled to the forward portion by the articulating adjustment means, and a head gripping pad pivotally coupled to an end of the rearward portion by an articulating means, the combination of which forms the support arm assemblies.

The articulating adjustment means preferably comprises cylindrical tongues or posts joined to the ends of the support arms, and sockets joined to each articulating head gripping pads which are structured and configured to pivotally engage the cylindrical posts on the support arms. In the second embodiment of the invention, the articulating means additionally comprises sockets on the articulating members which pivotally receive the posts on the fixed portion of the support arms, and posts on the articulating members which pivotally engage the sockets on the head gripping pads. A plurality of teeth or serrations may be provided on the outer surface of the posts and the inner surface of the sockets, with the teeth on the posts structured and configured to reversibly intermesh with the teeth of the sockets to provide pivotal articulation in a ratcheting fashion. The articulating adjustment means may alternatively comprise a ball and socket type hinge assembly connecting the support arms to the articulating members and/or articulating head gripping pads.

The invention is utilized by placing it on the wearer's head with the wearer's head generally positioned between the first and second support arm assemblies. The articulating members and/or articulating head gripping pads are pivotally adjusted to desired positions to accommodate the wearer's head by pushing on or otherwise applying force to the articulating members and/or head gripping pads. The amount of tension applied to the wearer's head by the first and second support arm assemblies is controlled by pivotally adjusting the position of the articulating members, or the head gripping pads, or both, depending upon the embodiment of the invention used. Optionally, the articulating members and head gripping pads are detachable and interchangeable so that the wearer can adjust or control the size of the visor and amount of head contact surface area by selecting particular articulating members and head gripping pads.

An object of the invention is to provide a head visor having rearwardly disposed tails which may be pivotally adjusted to fit the head of individual wearers.

Another object of the invention is to provide a head visor which is comfortable to wear for extended periods of time.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more specifically to the drawings, for illustrative purposes the present invention is embodied in the apparatus generally shown in FIG. 1 through FIG. 6. It will be appreciated that the apparatus may vary as to configuration and as to details of the parts without departing from the basic concepts as disclosed herein.

Figure 1:
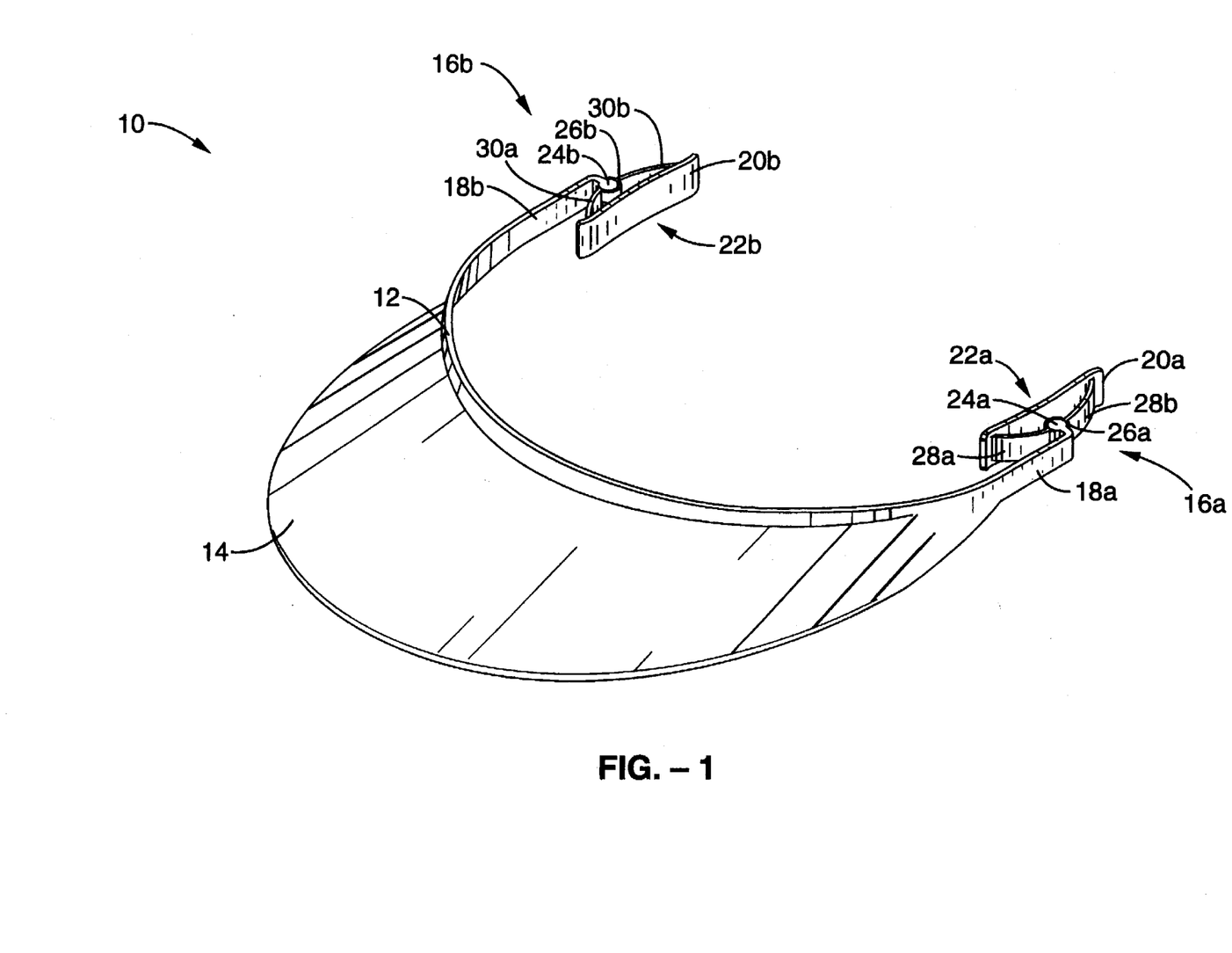
FIG. 1 is a perspective view of an articulating visor apparatus in accordance with the present invention.
Figure 2:
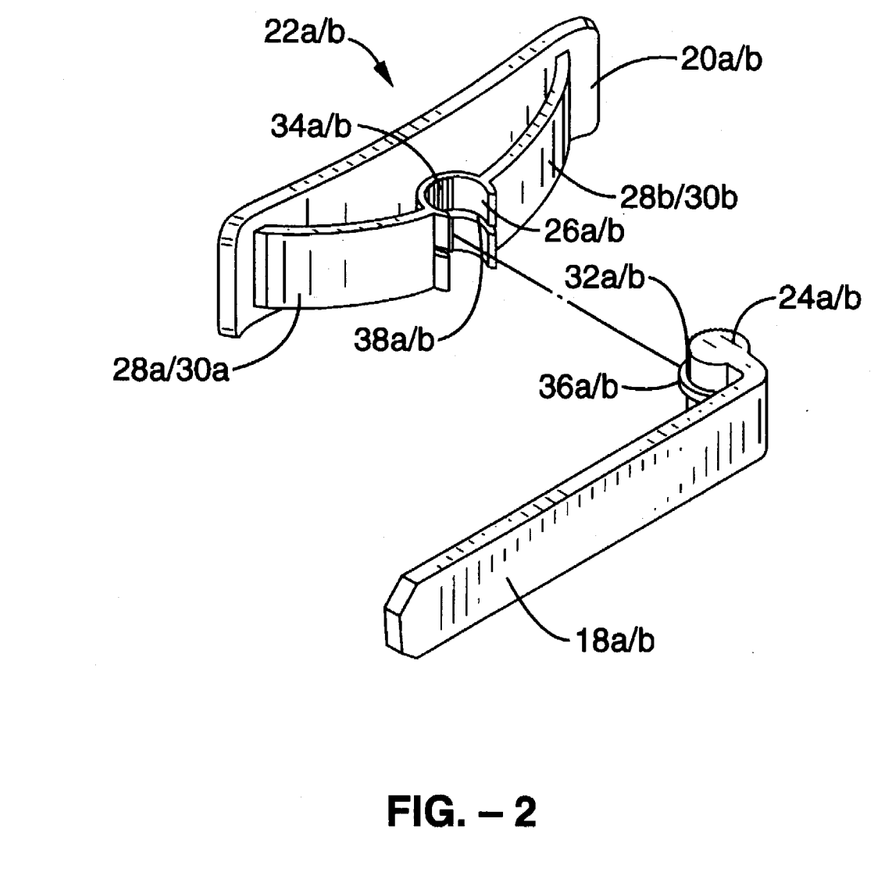
FIG. 2 is a detailed fragmentary view of the articulating adjustment means employed in the apparatus shown in FIG. 1.

Referring first to FIG. 1 and FIG. 2, an articulating visor apparatus 10 in accordance with the invention is generally shown. Visor 10 generally includes a headband 12, a forwardly disposed bill or shade 14 joined to head band 12, and a pair of rearwardly disposed support arm assemblies 16a, 16b. Headband 12, shade 14 and the forward portion of support arm assemblies 16a, 16b may be integrally formed from a single piece of resilient material such as polyethylene sheet, or may comprise separate portions which are joined together by adhesives, melt bonding, or like means.

First support arm assembly 16a generally includes a fixed or stationary forward portion or member, shown generally as support arm 18a, and a movable or articulating portion or member shown as head gripping pad 20a. Second support arm assembly 16b likewise includes a generally fixed support arm 18b and a movable or articulating head gripping pad 20b. Head gripping pads 20a, 20b preferably include curved inner surfaces 22a, 22b respectively which are structured and configured to conform generally to the shape of the wearer's head. The size, shape, structure, and configuration of support arms 18a, 18b and head gripping pads 20a, 20b may be varied as required for different wearer head sizes and different applications of the invention. As shown, support arms 18a, 18b are generally longer than head gripping pads 20a, 20b. However, head gripping pads 20a, 20b could alternatively be elongated relative to support arms 18a, 18b. Also, the surface area of curved inner surfaces 22a, 22b on head gripping pads 20a, 20b may be varied to control the amount of surface area in contact with the wearer's head. Further, cushioning means or sweat absorption means (not shown) may be included on head gripping pads 20a, 20b if desired. Additionally, if lesser comfort is acceptable, head gripping pads 20a, 20b can be replaced with generally straight, elongated articulating members to grip the wearer's head.

The articulating means for positionally adjusting head gripping pads 20a, 20b relative to support arms 18a, 18b and the wearer's head are provided with the invention preferably comprises first and second generally cylindrical posts 24a, 24b which are attached to the ends of first and second support arms 18a, 18b, respectively, and first and second sockets 26a, 26b attached to first and second head gripping pads 20a, 20b, respectively. Sockets 26a, 26b are structured and configured to pivotally engage or receive posts 24a, 24b. Preferably, socket 26a is coupled to head gripping pad 20a by connecting supports 28a, 28b, and socket 24b is coupled to head gripping pad 20b by connecting supports 30a, 30b. Connecting supports 28a, 28b and 30a, 30b are preferably constructed of resilient material. The location of posts 24a, 24b and sockets 26a, 26b may be interchanged, if desired, with posts 24a, 24b associated with head gripping pads 20a, 20b, and sockets 26a, 26b located at the ends of support arms 18a, 18b.

Referring more particularly to FIG. 2, a plurality of teeth or serrations 32a, 32b are included on the outer surface of posts 24a, 24b, and a corresponding plurality of teeth or serrations 34a, 34b are included on the inner surface of sockets 26a, 26b. Teeth 32a, 32b on posts 24a, 24b are structured and configured to reversibly intermesh with teeth 34a, 34b on sockets 26a, 26b to provide ratcheting pivotal articulation to head gripping pads 20a, 20b, as discussed further below. Teeth 32a, 32b, and 34a, 34b may be omitted if desired to allow smooth articulating motion of sockets 26a, 26b relative to posts 24a, 24b rather than a ratcheting articulating motion. Preferably, annular ridges 36a, 36b extend laterally around posts 24a, 24b respectively, and generally circular slob or grooves 38a, 38b are provided on sockets 26a, 26b, with slots 38a, 38b structured and configured to slidably receive ridges 36a, 36b on posts 24a, 24b. Ridges 36a, 36b and slots 38a, 38b prevent sockets 26a, 26b from sliding off of posts 24a, 24b respectively. Additional details on the foregoing coupling mechanism and various alternatives can be found in U.S. Pat. No. 5,503,497 issued on Apr. 2, 1996 owned by the assignee hereof, which is incorporated by reference herein.

Visor 10 is utilized by placing first and second support arm assemblies 16a, 16b about the sides of a wearer's head such that head band 12 and support arm assemblies 16a, 16b partially encircle the wearer's head, with shade 14 extending outward over the wearer's face. Preferably, support arms 18a, 18b are made of resilient polymeric material to tensionally engage the wearer's head and hold the apparatus thereon. Head gripping pads 20a, 20b are placed about the wearer's head and positioned comfortably on the wearer's head by pivotally adjusting head gripping pads 20a, 20b relative to support arms 18a, 18b and the wearer's head. The positional adjustment is made by applying suitable force or pressure to head gripping pads 20a, 20b, causing teeth 34a, 34b in sockets 26a, 26b to disengage from teeth 32a, 32b on posts 24a, 24b, allowing sockets 26a, 26b to pivot relative to posts 24a, 24b, and thus allowing articulating adjustment of head gripping pads 20a, 20b relative to support arms 18a, 18b and the wearer's head. When the position adjusting force or pressure is removed from head gripping pads 20a, 20b, teeth 32a, 32b and 34a, 34b re-engage and intermesh in the adjusted position and serve to retain the adjusted position. Ridges 36a, 36b remain in slots 38a, 38b during pivotal motion of sockets 26a, 26b and posts 24a, 24b relative to each other, and prevent posts 24a, 24b from slipping out of sockets 26a, 26b. Head gripping pads 20a, 20b thus allow articulating adjustment so as to provide for greater wearer comfort than can be achieved with conventional head visor devices. Preferably, sockets 26a, 26b are resilient, and posts 24a, 24b reversibly snap fit into sockets 26a, 26b. Thus, head gripping pads 20a, 20b may be detached from support arms 18a, 18b for cleaning, or interchanged with different sized and/or shaped head gripping pads or other movable members having suitable sockets thereon for pivotally engaging posts 24a, 24b.

Figure 3:
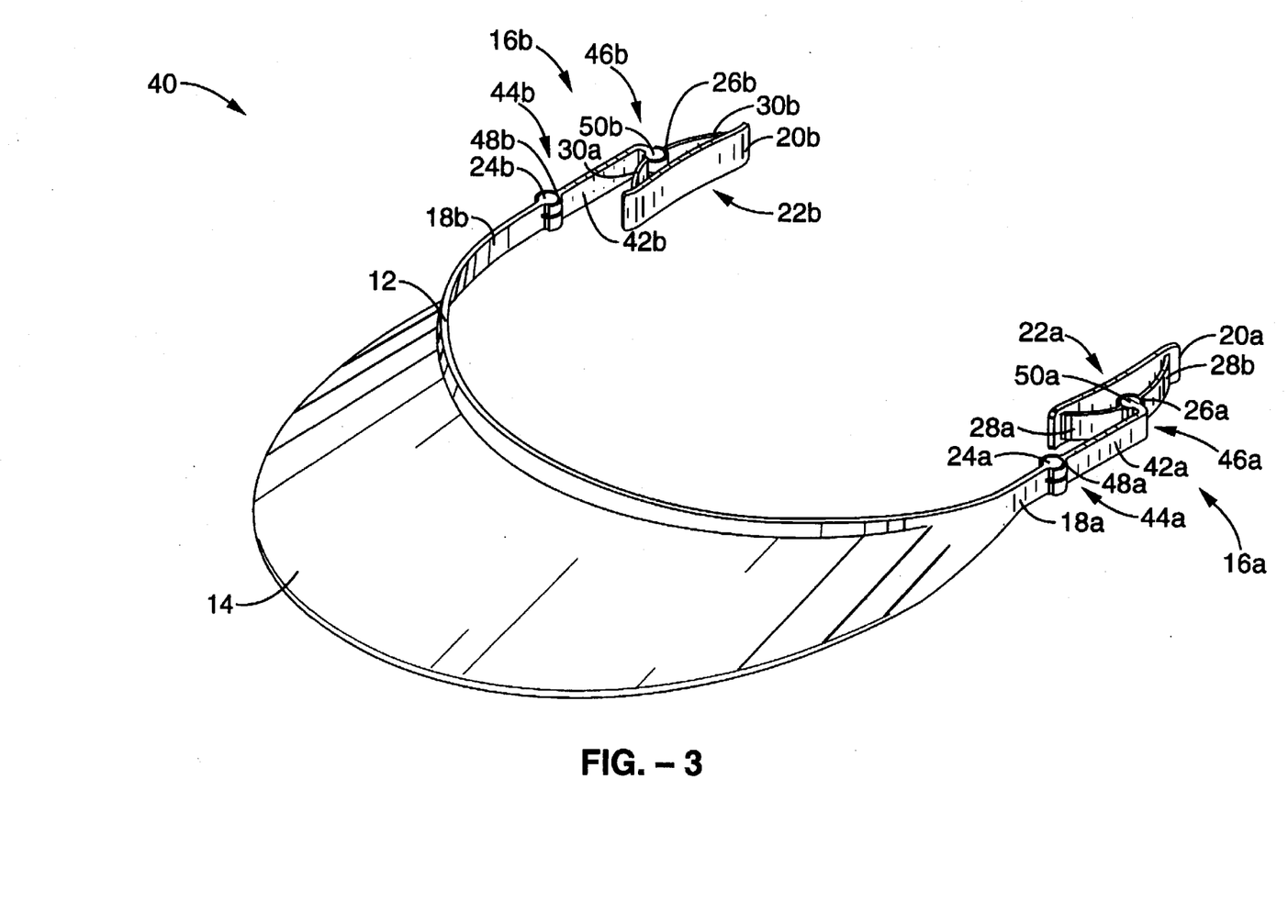
FIG. 3 is a perspective view of an alternative embodiment of the articulating visor apparatus shown in FIG. 1.
Figure 4:
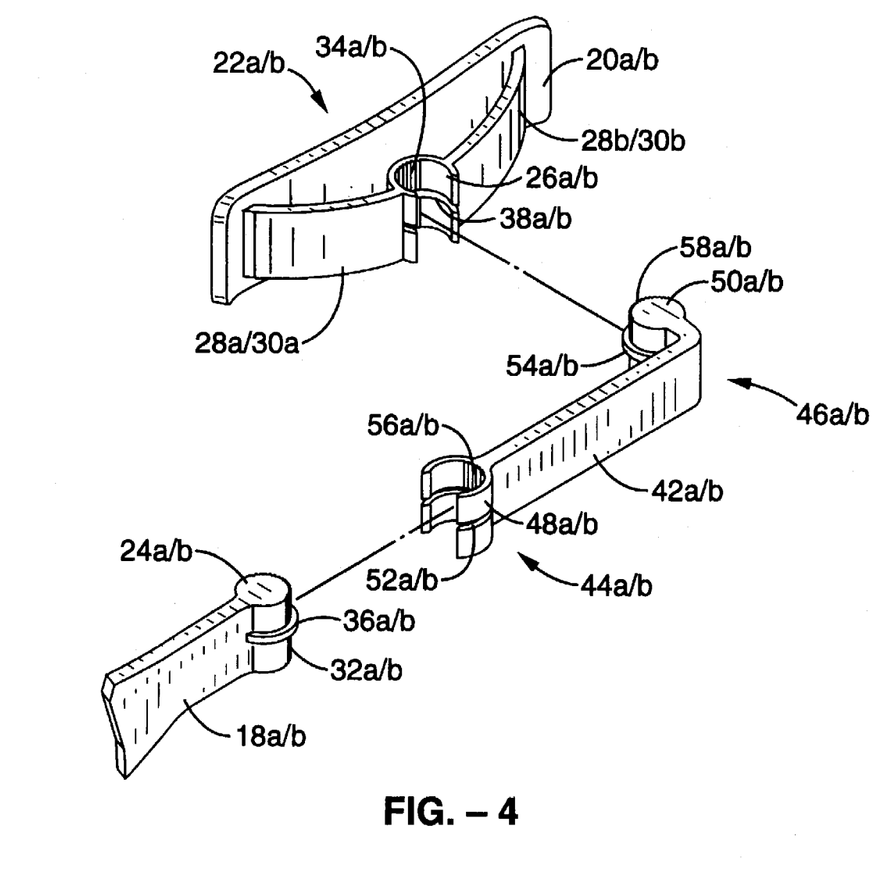
FIG. 4 is a detailed fragmentary view of the articulating adjustment means employed in the apparatus shown in FIG. 3.

Referring now to FIG. 3 and FIG. 4, there is shown an alternative embodiment 40 of an articulating visor apparatus in accordance with the present invention, wherein like reference numerals denote like parts. As in the first embodiment related above, visor 40 includes a headband 12, forwardly disposed shade 14, and a pair of rearwardly disposed support arm assemblies 16a, 16b. However, in this embodiment, support arm assemblies 16a, 16b each generally comprise fixed support arms 18a, 18b, articulating members 42a, 42b that are pivotally coupled to support arms 18a, 18b, respectively, and head gripping pads 20a, 20b that are pivotally coupled to articulating members 42a, 42b, respectively.

Preferably, articulating members 42a, 42b are of generally elongate shape as shown. Articulating member 42a has a first or front end 44a and a second or back end 46a, and articulating member 42b likewise includes a first or front end 44b and a second or back end 46b. A socket 48a is joined to first end 44a of articulating member 42a, and a generally cylindrical post 50a is coupled to second end 46a of articulating member 42a. Similarly, a socket 48b is attached to first end 44b of articulating member 42b, and a generally cylindrical post 50b is attached to second end 46b of articulating member 42b. Sockets 48a, 48b are structured and configured to pivotally engage posts 24a, 24b on support arms 18a, 18b, and posts 50a, 50b are structured and configured to pivotally engage sockets 26a, 26b on head gripping pads 20a, 20b. The length, structure and configuration of articulating members 42a, 42b may be varied as required for different wearer head sizes or for particular applications of the invention.

Referring more particularly to FIG. 4, sockets 48a, 48b each include a lateral slot 52a, 52b respectively, which slidably receive lateral ridges 36a, 36b on posts 24a, 24b respectively and prevent posts 24a, 24b from sliding out of sockets 48a, 48b. Posts 50a, 50b include lateral ridges 54a, 54b which engage slots 38a, 38b in sockets 26a, 26b and prevent posts 50a, 50b from sliding out of sockets 26a, 26b. A plurality of teeth or serrations 56 are included on the inner surface of sockets 48a, 48b, with teeth 56 structured and configured to reversibly engage and intermesh with teeth 32 on posts 24a, 24b. A plurality of teeth or serrations 58 are also provided on the outer surface of posts 50a, 50b, with teeth 58 structured and configured to reversibly engage teeth 34 in sockets 26a, 26b. It will be appreciated that the articulating couplings are the same as described above with regard to the embodiment shown in FIG. 1 and FIG. 2.

Figure 5:
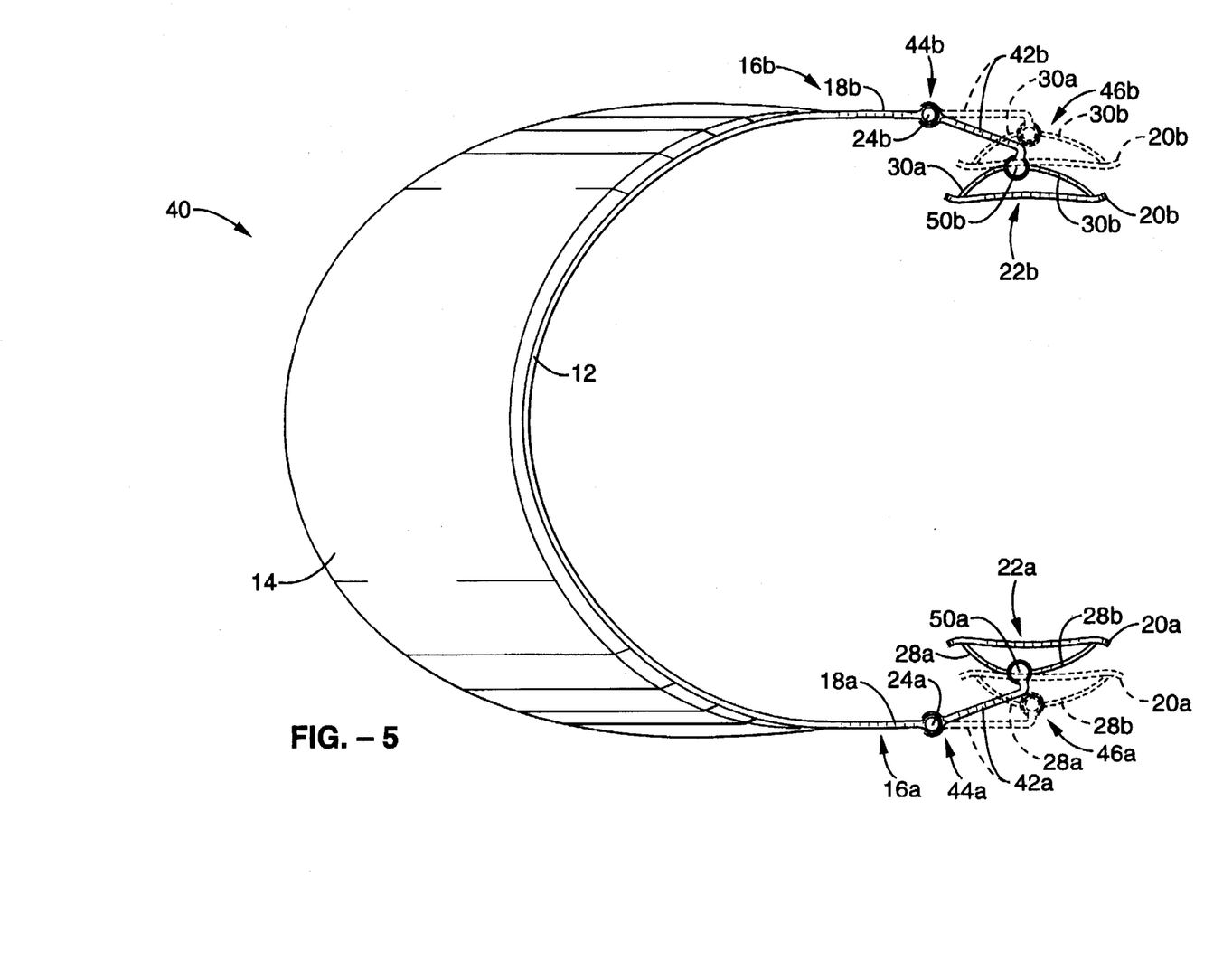
FIG. 5 is a top plan view of the articulating tail visor apparatus shown in FIG. 3, diagrammatically showing articulation of the moveable portions of the tails.

Referring also to FIG. 5, visor 40 operates in a similar manner to that described above for visor 10, with the primary difference between the two embodiments being that two points of pivotal articulation are provided on each of first and second support arm assemblies 16a, 16b. The wearer of visor 40 can positionally adjust head gripping regions 20a, 20b relative to his or her head by applying force to head gripping regions 20a, 20b, so that sockets 26a, 26b pivot or rotate about posts 50a, 50b respectively. Teeth 34a, 58a and 34b, 58b disengage and re-intermesh to retain the adjusted position as described above. Articulating members 42a, 42b likewise can be positionally adjusted by suitable application of pressure or force thereto such that sockets 48a, 48b on articulating members 42a, 42b pivot or rotate about posts 24a, 24b on support arms 18a, 18b respectively, with teeth 32a, 56a and 32b, 56b disengaging during positioning and re-engaging to retain the adjusted position. Positional adjustment of articulating members 42a, 42b in an inward direction towards the wearer's head applies greater tensional force to head gripping pads 20a, 20b, allowing the wearer to more firmly affix the visor 10 on the wearer's head. A looser fit is achieved by positionally adjusting articulating members 42a, 42b outward or away from the wearer's head. Thus, through the articulating motion of the movable portions of tails 16a, 16b, the wearer can precisely fit the head visor 40 to his or her head to provide maximum comfort.

Sockets 48a, 48b, as well as sockets 26a, 26b are preferably made of resilient material so that posts 50a, 50b reversibly snap fit into sockets 48a, 48b, allowing articulating members 42a, 42b to be disassembled from support arms 18a, 18b for cleaning or interchanging with other articulating members of different length or configuration. Posts 24a, 24b and sockets 48a, 48b are structured and configured so as not to protrude towards the wearer's head in a manner which could cause discomfort.

Additionally, as can be seen in FIG. 5, sockets 26a, 26b on head gripping pads 20a, 20b, respectively, are offset from the longitudinal center of the head gripping pads. This configuration, which is common to both visor 10 and visor 40, allows the wearer to make the overall tail length, and hence the visor length, longer or shorter by removing the head gripping pads, turning them over, and then reinstalling them. While the length change may be small, it can effect a significant change in comfort to the wearer. Note also that the back ends 46a, 46b of articulating members 42a, 42b are arcuately offset from the longitudinal axis of the members to allow for a greater range of pivotal movement of head gripping pads 20a, 20b before contacting articulating members 42a, 42b. This offset configuration is also preferable on the ends of support arms 18a, 18b of visor 10 shown in FIG. 1 and FIG. 2.

Note also that visor 40 may be used without head gripping pads 20a, 20b, if desired. When omitting head gripping pads 20a, 20b, posts 50a, 50b on second ends 44a, 44b of articulating members 42a, 42b are also preferably omitted. In this arrangement it is also preferably to provide a slightly curved head-accommodating shape or inner surface to articulating members 42a, 42b to increase wearer comfort. Cushioning means and/or sweat absorption means may also be used in association with articulating members 42a, 42b.

Figure 6:
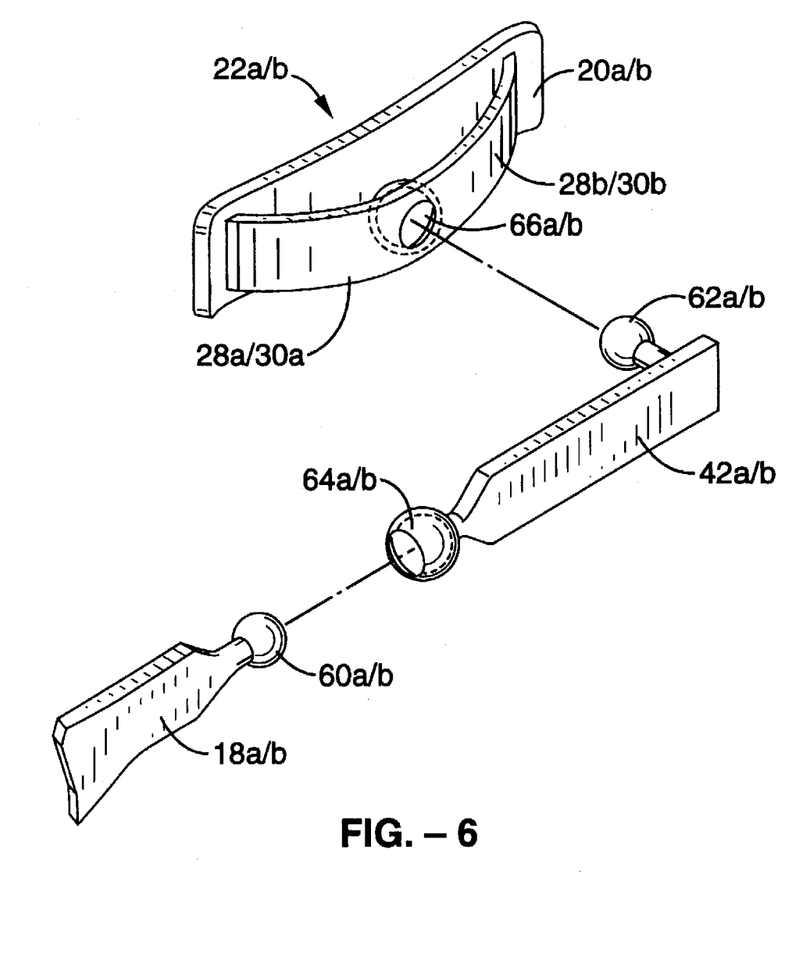
FIG. 6 is a detailed fragmentary view of an alternative embodiment of the articulating adjustment means employed in the present invention.

Referring to FIG. 6, the articulating means employed in the visors described above may alternatively comprise ball and socket hinge means. For example, it is contemplated that posts 24a, 24b and 50a, 50b may be replaced with generally hemispherical ball joints 60a, 60b and 62a, 62b, and that sockets 26a, 26b and 48a, 48b could be replaced with corresponding ball sockets 64a, 64b and 66a, 66b to receive the ball joints. The use of ball and socket articulating means with the invention allows vertical as well as horizontal pivotal adjustment as described above, so that shade 14 may be pivoted up and down relative to the wearer's face without removing the visor from the wearer's head. Other standard hinge arrangements are also contemplated for use with the invention.

Accordingly, it will be seen that this invention provides a head visor apparatus having articulating tails which allow a greater degree of positional adjustment and wearer comfort than has heretofore been available. Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. An articulating head worn visor apparatus, comprising,
   (a) a headband;
   (b) a forwardly disposed shade coupled to said headband;
   (c) a first rearward extending support arm assembly, said first support arm assembly including a first support arm coupled to said headband and a first head gripping member coupled to said first support arm;
   (d) a second rearward extending support arm assembly, said second support arm assembly including a second support arm coupled to said headband and a second head gripping member coupled to said second support arm;
   (e) a first articulating member positioned between said first support arm and said first head griping member, said first articulating member including a first end and a second end, said first end of said first articulating member pivotally coupled to said first support arm, said second end of said first articulating member pivotally coupled to said first head gripping member; and
   (f) a second articulating member positioned between said second support arm and said second head griping member, said second articulating member including a first end and a second end, said first end of said second articulating member pivotally coupled to said second support arm, said second end of said second articulating member pivotally coupled to said second head gripping member.

2. A head worn visor apparatus, comprising,
   (a) a headband;
   (b) a forwardly disposed shade coupled to said head band;
   (c) first and second rearwardly disposed support arms coupled to said headband, said first and second support arms each including a rearward end; and
   (d) first and second articulating members, said first and second articulating members each including a forward and rearward end, said forward end of said first articulating member pivotally coupled to said rearward end of said first support arm, said forward end of said second articulating member pivotally coupled to said rearward end of said second support arm.

3. An apparatus as recited in claim 2, further comprising first and second head gripping members, said first head gripping member pivotally coupled to said rearward end of said first articulating member, said second head gripping member pivotally coupled to said forward end of said second articulating member.

4. An apparatus as recited in claim 3, further comprising;
   (a) first and second cylindrical posts, said first post coupled to said rearward end of said first support arm, said second post coupled to said rearward end of said second support arm; and
   (b) first and second sockets, said first socket coupled to said forward end of said first articulating member, said first socket structured and configured to pivotally engage said first post, said second socket coupled to said forward end of said second articulating member, said second socket structured and configured to pivotally engage said second post.

5. An apparatus as recited in claim 4, further comprising:
   (a) third and fourth cylindrical posts, said third post coupled to said rearward end of said first articulating member, said fourth post coupled to said rearward end of said second articulating member; and
   (b) third and fourth sockets, said third socket coupled to said first head gripping member, said third socket structured and configured to pivotally engage said third post, said fourth socket coupled to said second head gripping member, said fourth socket structured and configured to pivotally engage said fourth post.

* * * * *

UNITED STATES PATENT AND TRADEMARK OFFICE
Certificate

Patent No. 5,682,608            Patented: November 4, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Timothy J. Landis, Roseville, CA; and Clay Allen, Elk Grove, CA.

Signed and Sealed this Second Day of April 2002.

PETER P. NERBUN
*Acting Supervisory Patent Examiner*
Art Unit 3765